United States Patent [19]
Rowland

[11] Patent Number: 5,405,613
[45] Date of Patent: Apr. 11, 1995

[54] VITAMIN/MINERAL COMPOSITION

[75] Inventor: David Rowland, Nobel, Canada

[73] Assignee: Creative Nutrition Canada Corp., Uxbridge, Canada

[21] Appl. No.: 8,225

[22] Filed: Jan. 22, 1993

Related U.S. Application Data

[63] Continuation of Ser. No. 806,935, Dec. 11, 1991, abandoned.

[51] Int. Cl.⁶ ............................................. A61K 47/00
[52] U.S. Cl. .................. 424/439; 424/195.1; 514/904; 514/905
[58] Field of Search ............ 424/440, 195.1, 439; 514/904, 905

[56] References Cited

U.S. PATENT DOCUMENTS

| | | | |
|---|---|---|---|
| 4,751,085 | 6/1988 | Gaull | 424/145 |
| 4,752,479 | 6/1988 | Briggs | 424/472 |
| 4,851,431 | 7/1989 | Yehuda | 514/560 |
| 4,871,550 | 10/1989 | Millman | 424/601 |
| 4,976,960 | 12/1990 | Grossman | 424/195.1 |

FOREIGN PATENT DOCUMENTS 0937150  9/1963  United Kingdom .

OTHER PUBLICATIONS

Indian Materia Medica Chap. 13: Asphaltum at 23–32.
Burr & Lane "Electrical Characteristics of Living Systems" Yale J. Biol. and Med. 8:31 1939.
Burr & Northrop "Evidence for the Existence of an Electrodynamic Field in Living Organisms" Proc. Nat. Acad. Sci. 5:284, 1939.
Burr "The Meaning of Bio-Electric Potentials" Yale J. Biol. and Med. 16:353, 1944.

*Primary Examiner*—D. Gabrielle Phelan
*Attorney, Agent, or Firm*—Bereskin & Parr

[57] ABSTRACT

A composition comprising Shilajit or an extract thereof in a vitamin and/or mineral preparation. Shilajit is a compact mass of vegetable organic matter, composed of a gummy matrix interspersed with vegetable fibres and minerals. Substances which have been identified in Shilajit include moisture, gums, albuminoids, calcium, potassium, nitrogen, silica, resin, vegetable matter, magnesium, sulphur, iron, chloride, phosphorous, iodine, glycosides, tannic acid, benzoic acid and a number of vitamins and enzymes. The invention further relates to a method to restore energetic balance or intensity, or to support or enhance a bioenergetic field in a mammal comprising administering to a mammal an effective amount of Shilajit or an extract thereof.

7 Claims, 15 Drawing Sheets

FORMULA S.T.R.

FORMULA V.S.C.

VITAMIN/MINERAL COMPOSITION

This application is a continuation of application Ser. No. 07/806,935, filed on Dec. 11, 1991, now abandoned.

FIELD OF THE INVENTION

The present invention relates to the use of Shilajit or extracts thereof in vitamin and/or mineral compositions; to vitamin and/or mineral compositions containing Shilajit or extracts thereof; and, to methods to restore energetic balance or intensity, or to support or enhance a bioenergetic field in a mammal using Shilajit or extracts thereof.

BACKGROUND OF THE INVENTION

Over the past 50 years or so, scientists have become increasingly aware of biomagnetic energy which involves the electromagnetic energy generated by living cells, as well as subtle energetic fields, which interpenetrate and surround living organisms. (See for example Becker, R., and G. Sheldon, The Body Electric: Electromagnetism and the Foundation of Life, New York. William Morrow and Company Inc., 1985; H. S. Burr and C. T. Lane, in "Electrical Characteristics of Living Systems" ((1935) *Yale Journal of Biology and Medicine* 8:31; H. S. Burr and F. S. Northrop, "Evidence for the Existence of an Electrodynamic Field in Living Organisms" in *Proceedings of the National Academy of Sciences of the U.S.A.* 5:284; and, H. S. Burr, in "The Meaning of Bio-Electric Potentials" ((1944) *Yale Journal of Biology and Medicine* 16:353).

Vibrational medicine treats the human body by integrating and balancing the energetic systems which influence cellular patterns of manifestation. The basis for vibrational medicine is the finding that a series of interacting subtle energy systems help regulate cellular physiology. According to the theory of vibrational medicine, a person's body tends to resonate with one dominant energetic vibration and, when weakened or shifted from equilibrium, the body tends to oscillate at a different and less harmonious frequency. These imbalances can lead to dysfunction, and the restoration of balance assists the organism to regain its normal functioning. Anything which helps the body rebalance and-/or restore the intensity of its energy can thus have a positive effect on health.

Acupuncture, acupressure, and electroacupressure are examples of therapies which help to restore energetic balance. The techniques rely on influencing and balancing patterns of energy which express through meridians, or microtubular channels, which carry subtle energy to the various organs and tissues of the body. In the 1960's, Kim Bong Han discovered these microtubular channels, ranging in diameter from 0.5 to 1.5 microns using microautoradiography (S. Rose-Nell, "The Work of Professor Kim Bong Han", (1967) *The Acupuncturist* 1:15).

Other therapies which have been used to restore energetic balance and/or energetic intensity include magnetotherapy, ultrasonic therapy and homeopathy. Each of these techniques works by precipitating change in energy fields, which in turn stimulates change at the physical level. In homeopathy, a person ingests an extremely dilute solution of a substance, often so dilute that no molecules of the original substance remain. It appears that the energetic frequency of the substance, serves as the active part of the homeopathic remedy.

In the Eastern world, a compound known as Shilajit (silajit) has a history of use as a folk remedy for various disorders, including genito-urinary diseases, diabetes, gall stones, jaundice, enlarged spleen, fermentative dyspepsia, worms, digestive disorders, piles, epilepsy, nervous disorders, eczema, anaemia, anorexia, asthma etc. Shilajit has also been used as a tonic to help retain youthful vigour. Shilajit has been administered either by itself or in combination with certain other ayurvedic (herbal) medicines.

Shilajit is a natural exudate ejected from rocks during hot weather in the lower Himalayas, Vindhya and other mountain tracts and Nepal, or it may be a tar formed in the earth from the decomposition of vegetable substances. (See the Indian Materia Medica, pages 23 to 32 for a detailed discussion of the composition and properties of Shilajit). It is a compact mass of vegetable organic matter, composed of a gummy matrix interspersed with vegetable fibres and minerals. Substances which have been identified in Shilajit include moisture, gums, albuminoids, calcium, potassium, nitrogen, silica, resin, vegetable matter, magnesium, sulphur, iron, chloride, phosphorous, iodine, glycosides, tannic acid, and a number of vitamins and enzymes. Shilajit also contains benzoic acid, a compound which, along with its derivatives, has been used as a component of nutritional vitamin and mineral preparations.

SUMMARY OF THE INVENTION

The present inventor has found that Shilajit over and above its nutritional and herbal content has novel energetic properties. Measurement of subtle energy changes indicate that Shilajit has a vibratory field that is substantially stronger than any vitamin, mineral, food substance or herb. Its vibratory field is also stronger than the vibratory fields of any of the known ingredients which make up Shilajit, when these ingredients are tested as pure substances from non-Shilajit sources.

The present inventor has also surprisingly found that when a small amount of Shilajit is added to a vitamin or mineral preparation, the energetic properties of the vitamin or mineral preparation are enhanced. In particular, the present inventor has found that the addition of a small amount of Shilajit to a vitamin or mineral preparation increases the energy field of the entire preparation to at or near the vibratory level of pure Shilajit.

The addition of Shilajit to vitamin or mineral preparations imparts to the preparations an energetic quality above and beyond their nutritional content. As well, the energetic quality of Shilajit-fortified vitamin and mineral preparations support or enhance a user's bioenergetic field.

The present invention therfore relates to the use of Shilajit or extracts thereof in a vitamin and/or mineral preparation to enhance the energy properties of the preparation.

The invention also relates to a composition comprising Shilajit or extracts thereof in a vitamin and/or mineral preparation.

The invention further relates to a method to restore energetic balance or intensity, or to support or enhance a bioenergetic field in a mammal comprising administering to a mammal an effective amount of Shilajit or extracts thereof. Preferably, the Shilajit or extract thereof is administered in a vitamin and/or mineral preparation.

BRIEF DESCRIPTION OF THE DRAWINGS

The file of this patent contains at least one drawing executed in colour. Copies of this patent with colour drawing(s) will be provided by the Patent and Trademark Office upon request and payment of the necessary fee.

Further details of the invention are described below with the help of the examples illustrated in the accompanying drawings in which.

DETAILED DESCRIPTION OF THE INVENTION

Figure 1:
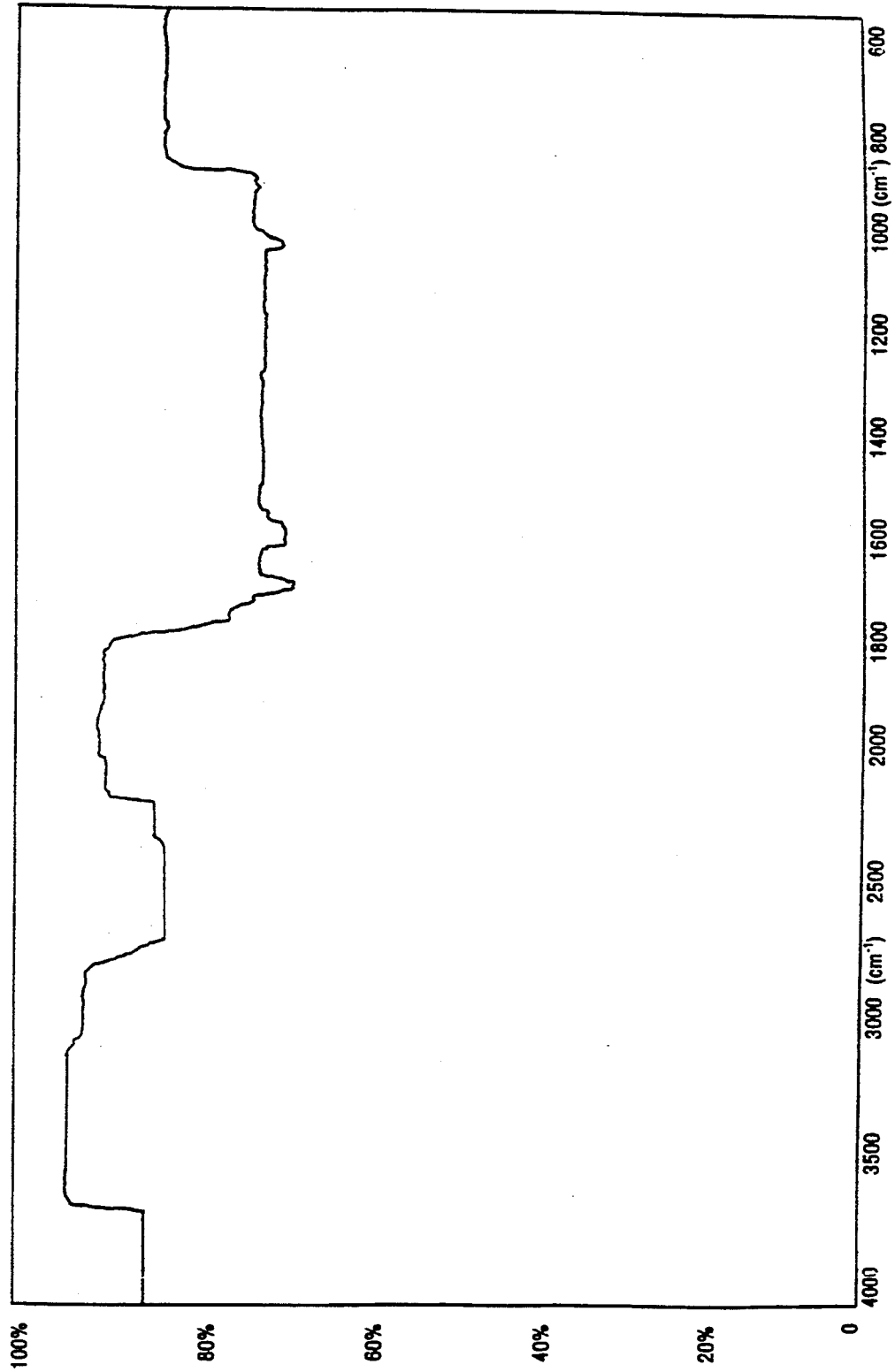
FIG. 1 is a gragh showing the transmission of infrared light by the Original Formula vitamin-mineral formulation.
Figure 2:
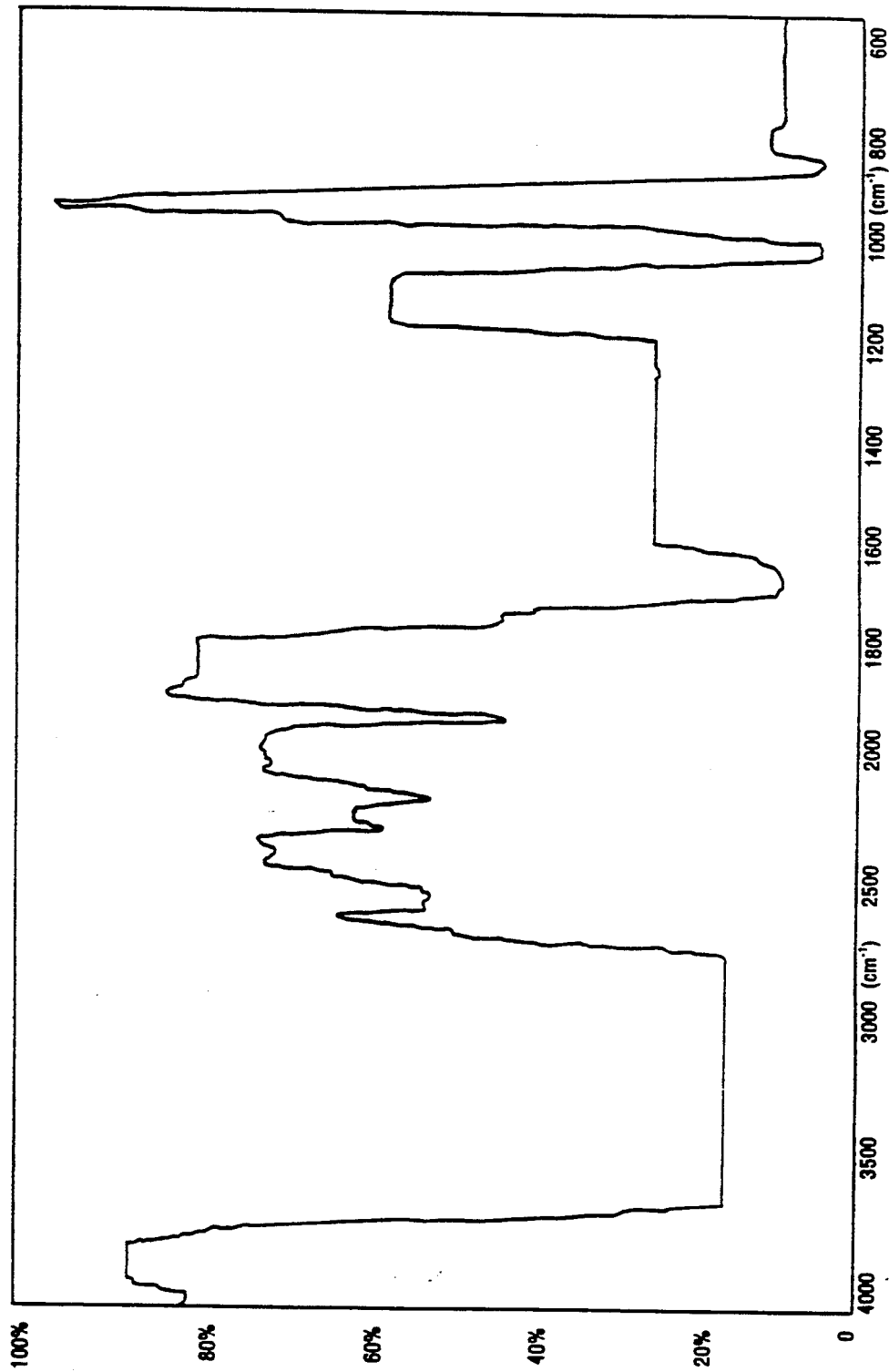
FIG. 2 is a gragh showing the transmission of infrared light by a sample containing the components of the Original Formula vitamin-mineral formulation and 13 mg of Shilajit.
Figure 3:
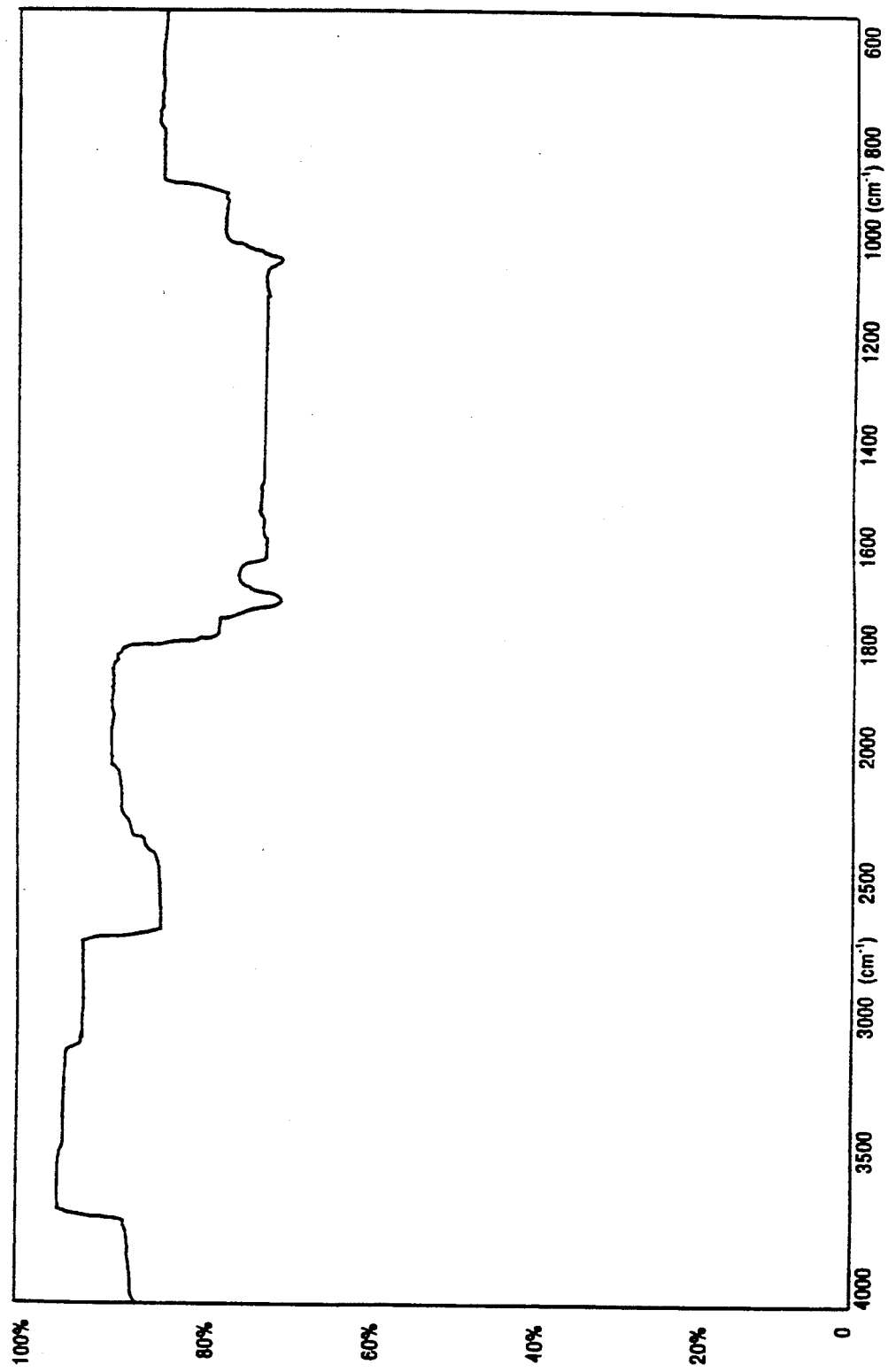
FIG. 3 is a gragh showing the transmission of infrared light by the Formula S.T.R. vitamin-mineral formulation.
Figure 4:
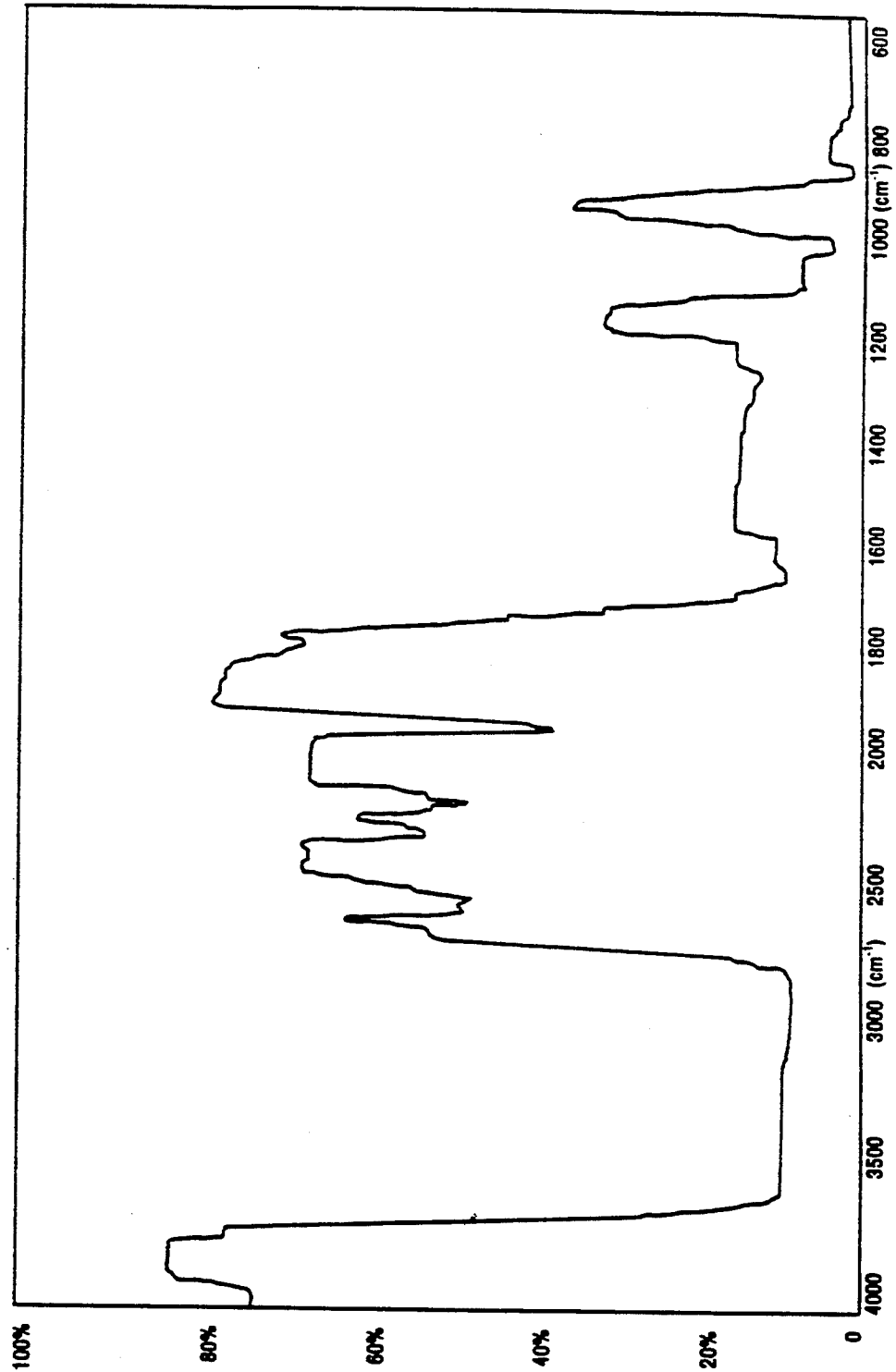
FIG. 4 is a gragh showing the transmission of infrared light by a sample containing the components of the Formula S.T.R. vitamin-mineral formulation and 13 mg of Shilajit.
Figure 5:
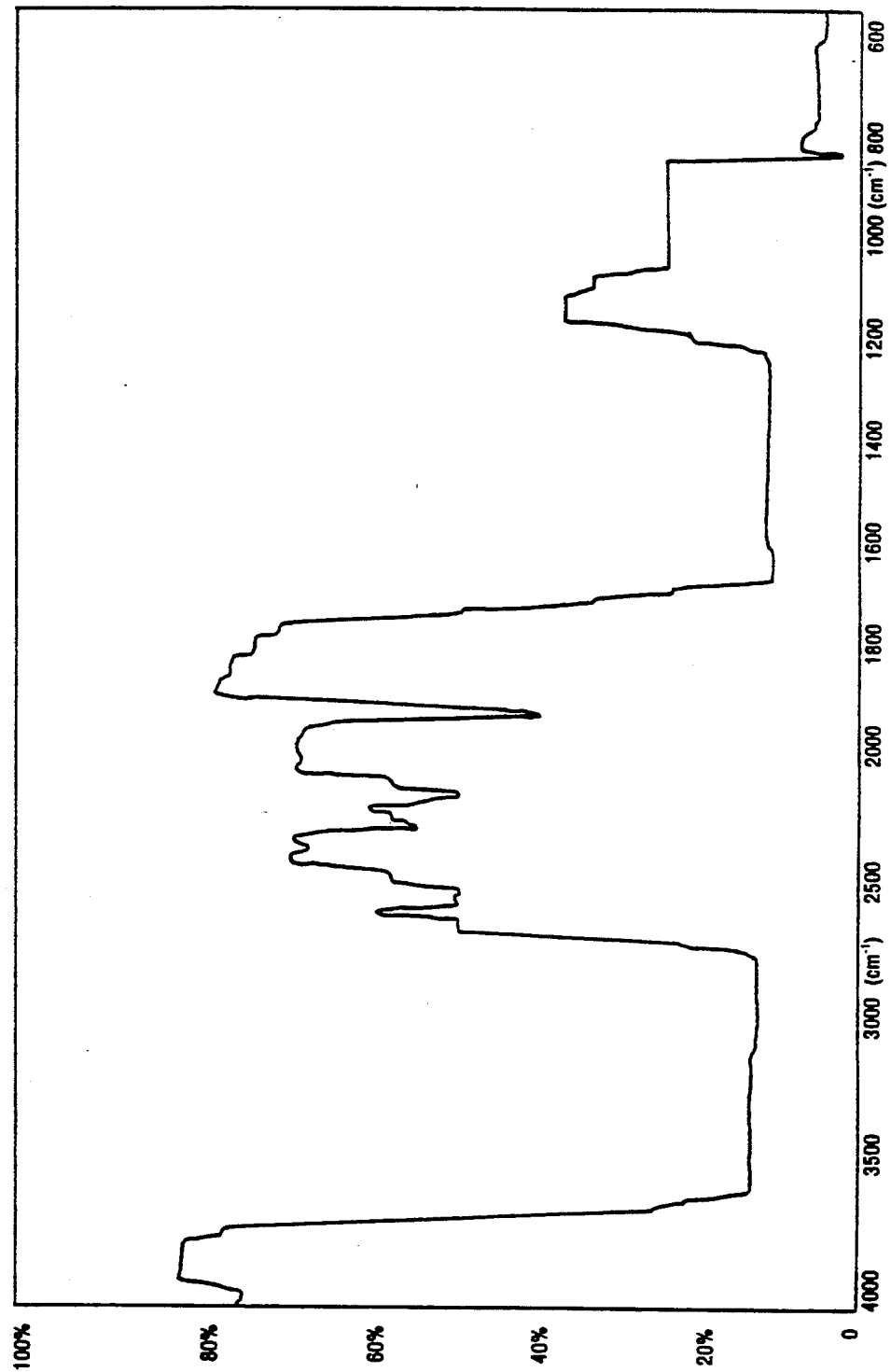
FIG. 5 is a gragh showing the transmission of infrared light by a sample containing the components of the Formula S.T.R. vitamin-mineral formulation and 40 mg of Shilajit.
Figure 6:
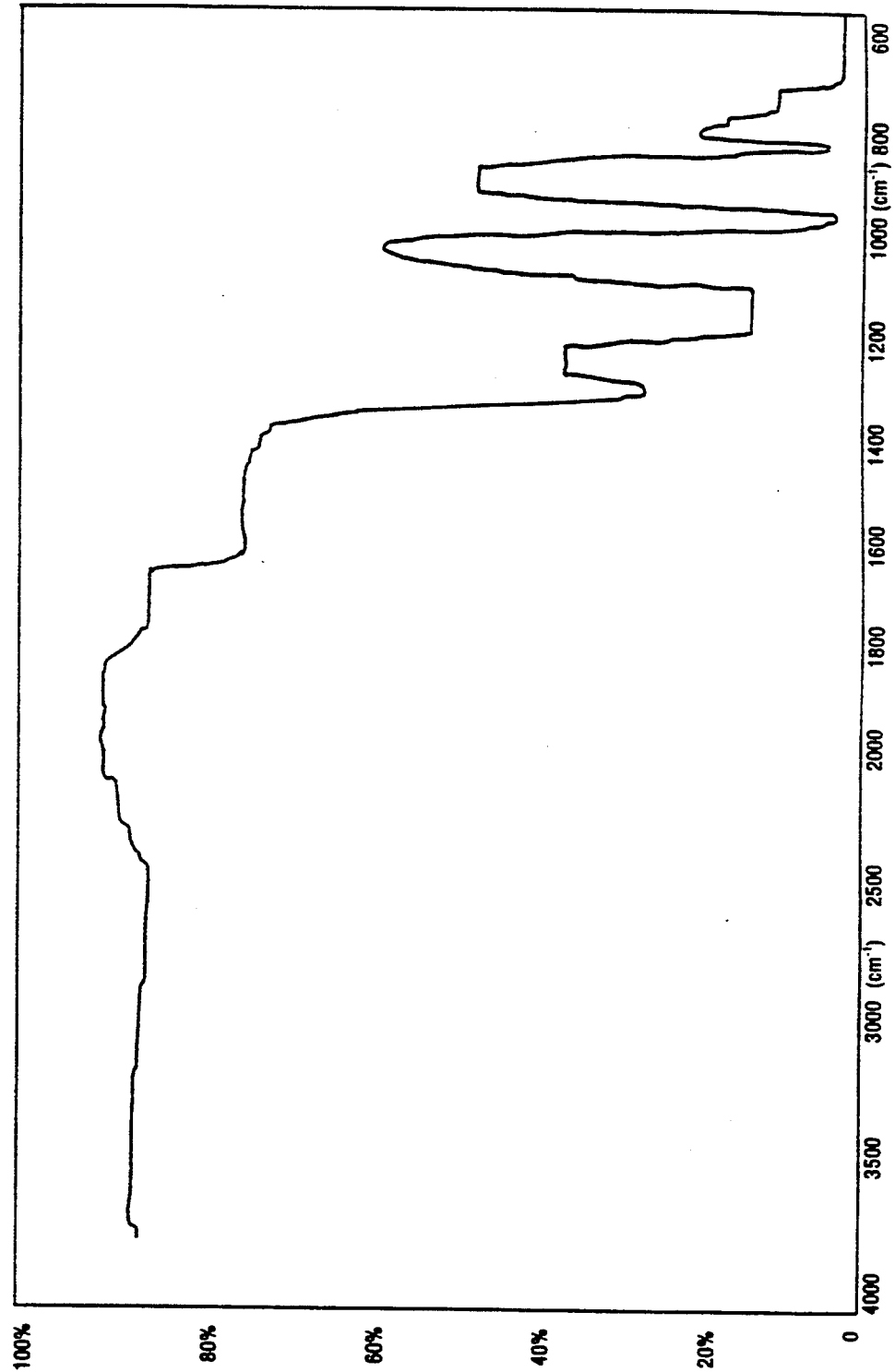
FIG. 6 is a gragh showing the transmission of infrared light by the Formula SUPER C-M-K vitamin-mineral formulation.
Figure 7:
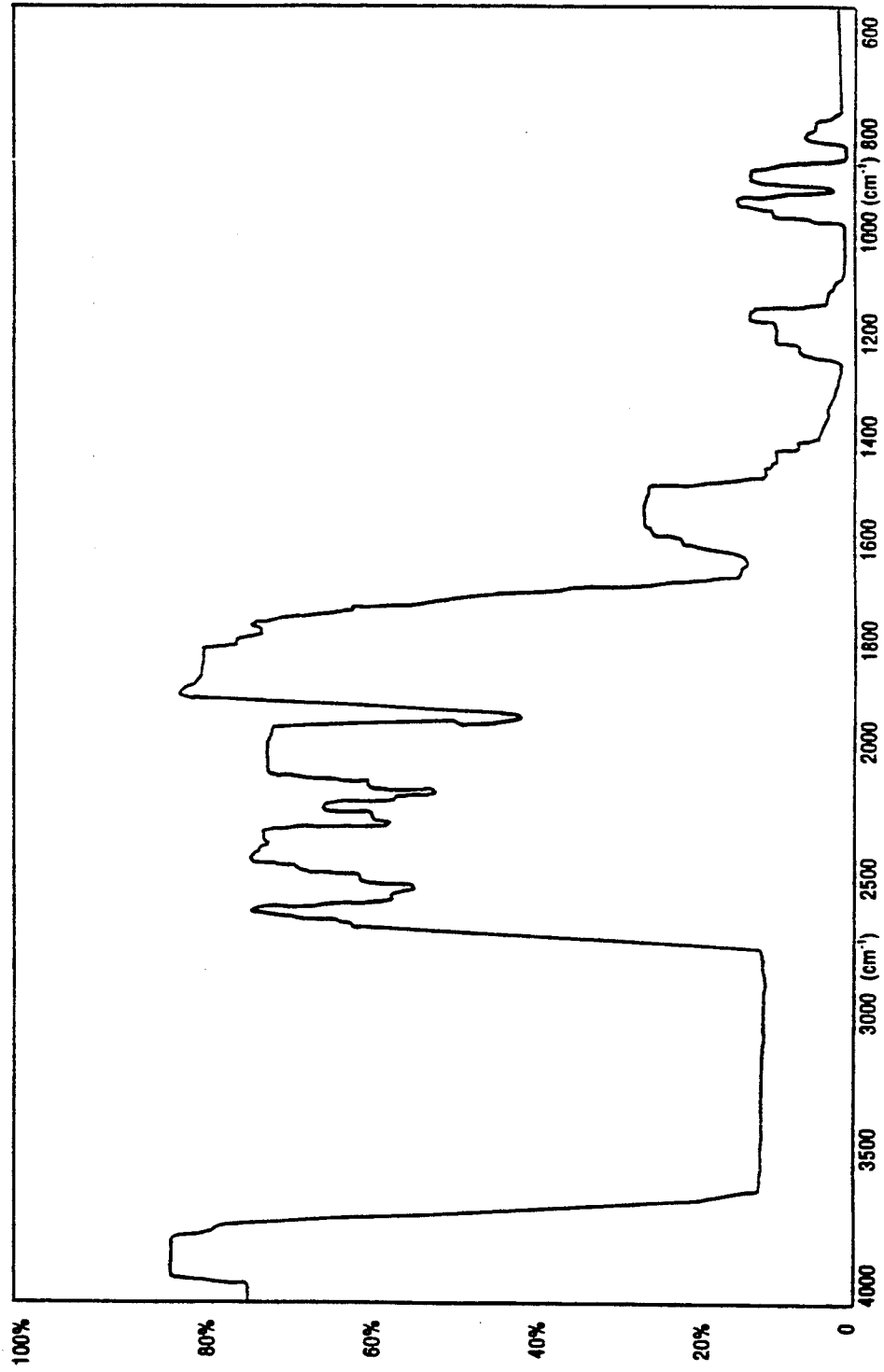
FIG. 7 is a gragh showing the transmission of infrared light by a sample containing the components of the Formula SUPER C-M-K vitamin-mineral formulation and 13 mg of Shilajit.
Figure 8:
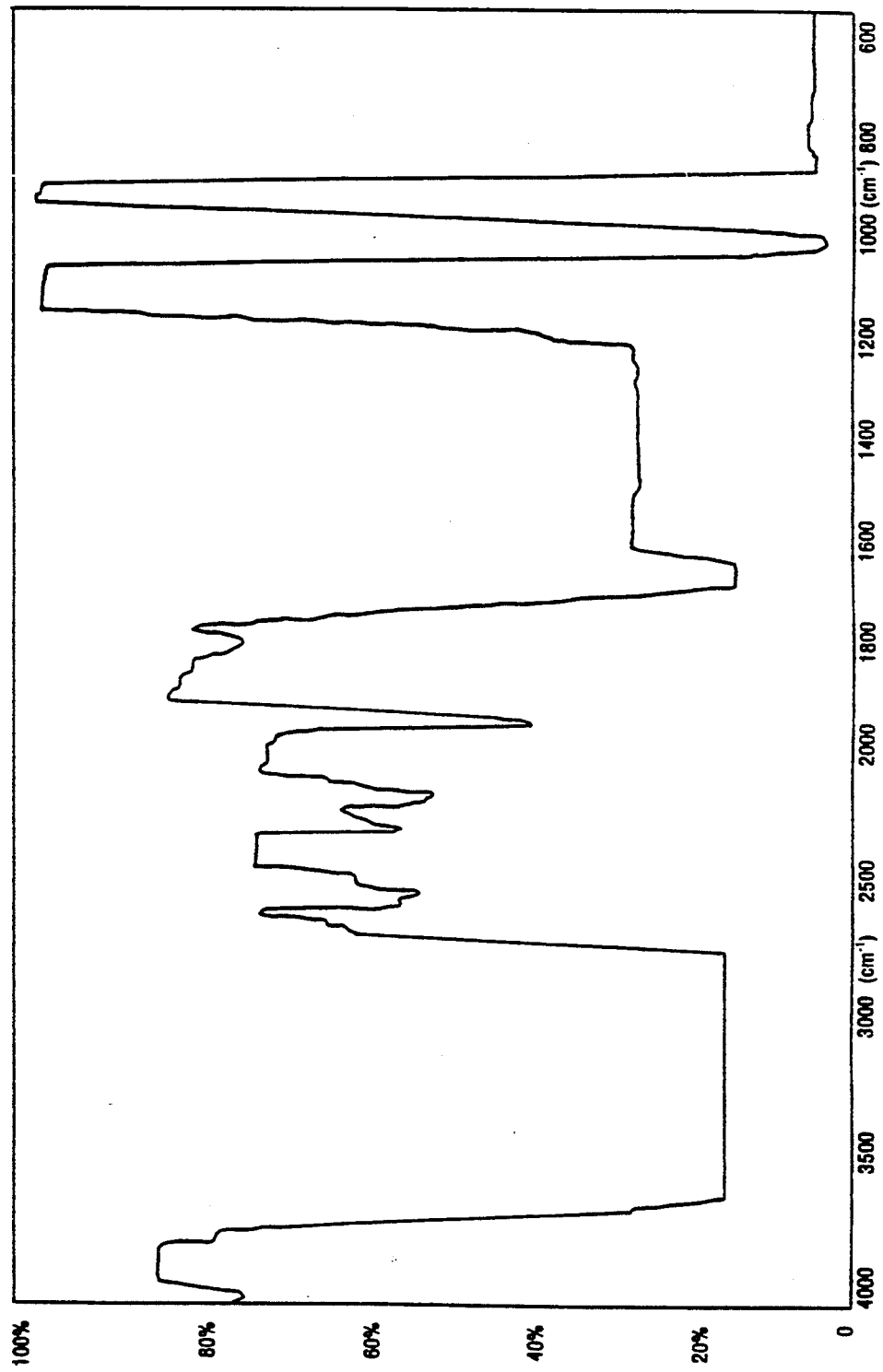
FIG. 8 is a gragh showing the transmission of infrared light by a sample containing the components of the Formula SUPER C-M-K vitamin-mineral formulation and 40 mg of Shilajit.

As hereinbefore mentioned, the present invention relates to the use of Shilajit or extracts thereof in a vitamin and/or mineral preparation to enhance the energy properties of the preparation. The invention also relates to a composition comprising Shilajit or extracts thereof in a vitamin and/or mineral preparation.

The vitamin and/or mineral preparation used in the invention and composition of the invention may be any commonly used vitamin and/or mineral preparation. The ingredients of an exemplary commonly used vitamin and/or mineral preparation are set forth in Table 1. It will be appreciated that a vitamin and/or mineral preparation which may be used in the present invention may not include all the ingredients set forth in Table 1 and ingredients other than those set forth in Table 1 may be included in the preparation. Preferably, the vitamin and/or mineral preparation has the components set forth in any one of Tables 2 to 6. The concentration of the vitamin and/or mineral components will depend on individual needs and on the desired effect. Concentrations of components which may be used in the vitamin and/or mineral preparation are set forth in Tables 2 to 6.

The Shilajit used in the invention and in the composition of the invention may be obtained as an exudate from rocks in the Himalayas. The Shilajit may be obtained commercially, for example, from Dabur India Limited, New Delhi, India. The Shilajit may have the constituents set out in Table 7. Extracts of Shilajit may also be used in the present invention. Preferably, the Shilajit used in the invention is the Shilajit known as "Iron Shilajit". Iron Shilajit is obtained by extracting raw Shilajit with purified water from the rocks from which it exudes. The extracted Shilajit is then treated with a mixture of three herbs known as trifla, which includes amla (*emblica officinalis*), bahera (*terminalia chebula*), and haritaki (*terminalia belerica*), to remove possible contaminants. The purified Shilajit which is obtained is then dehydrated to remove moisture. The Shilajit produced and refined by this method is almost totally sterile. Laboratory analysis reveals that it has a bacterial count of only 50 colonies per gram and a yeast-/fungus count of only 10 colonies per gram.

It will be appreciated that substances which have the energetic properties of Shilajit may also be used in the present invention. Such substances may be identified using the methods described in the examples herein. For example, a substance which has the energetic properties of Shilajit may be identified by determining the degree of oscillation of the substance using a Cameron Aurameter (See Example 1).

The concentration of Shilajit in the composition of the invention will depend on individual needs and on the desired effect. The concentration of the Shilajit in the composition of the invention may be from about 0.4% to 10%, and preferably about 1% to 3%, most preferably 1% to 2% by weight of the composition.

In a preferred embodiment of the invention, the composition of the invention includes but is not limited to the components set out in Table 4 herein with 1% to 2% by weight of Shilajit.

The composition of the invention may be prepared by mixing the various components of the composition using conventional methods. In particular, the various components of the composition of the invention may be mixed in powder form and/or encapsulated and/or pressed into solid form preparations such as tablets or pills. The preferred composition of the invention may be prepared according to the constituent ranges set forth herein in Table 1.

The invention also relates to enhanced embodiments of the composition of the invention which include the composition described above containing other additives. Examples of such additives are flavoring and coloring agents, lipotropic factors, amino acids, glandular concentrates, bioflavanoids, phospholipids, para amino benzoic acid, sorbitol, betaine hydrochloride, N-N-dimethylglycine, herbs, pectin, cellulose, di-calcium phosphate, silica gel, stearic acid and magnesium stearate.

The compositions of the invention are intended for administration to humans or animals.

The present invention also contemplates a method to restore energetic balance or intensity, or to support or enhance a bioenergetic field in a mammal comprising administering to a mammal an effective amount of Shilajit. Preferably the method is carried out through the use of the composition described above. The method of the invention may be used to restore energy balance or energy intensity or to support or enhance a bioenergetic field in a mammal particularly in cases where there has been energy dysfunction as a result of disease or trauma. The compositions of the invention may be particularly useful in conditions such as artherosclerosis, heart disease, physiological stress, hypoglycemia, adrenal weakness, arthritis, candidiasis, cancer, premenstrual syndrome, menopause, prostatitis, bacterial and viral infections, heavy metal accumulations, nicotine addiction, hypertension, muscle cramping, osteoporosis, hypothyroidism, nervous tension, anaemia and cataracts.

The following non-limiting examples are illustrative of the present invention:

EXAMPLES

EXAMPLE 1

The energetic properties of Shilajit-containing vitamin/mineral compounds were measured using a Cameron Aurameter. The instrument is a dowsing device developed by the Life Understanding Foundation of Santa Barbara, Calif. It consists of a metallic, weighted, spring-mounted pendulum connected to a handle by means of a vertically hinged mount. The unique mount enables the pendulum to oscillate either vertically or horizontally in a free-floating fashion.

The Cameron Aurameter is sensitive to subtle energy fields given off by both animate and inanimate objects. The instrument is operated as follows. The aurometer is held so that the pendulum is at complete rest. The device is then moved over the object to be tested. If sufficient energy is being given off by the object, the pendulum oscillates. The amplitude of the oscillation is directly proportional to the intensity of energy. In other words, the greater the distance taken by the pendulum in completing its stroke, the stronger the energy emanating from the object.

Five vitamin-mineral formulations distributed by Creative Nutrition Canada Corp. Uxbridge, Ontario, under the trade mark VITAMOST ® were tested using the above described method: FORMULA V.S.C. (Table 2), FORMULA S.T.R. (Table 3), ORIGINAL FORMULA (Table 4), FORMULA C.N.R. (Table 5) and SUPER C-M-K (Table 6). The composition of these vitamin-mineral formulations are shown in Tables 2-6, as indicated. For each of the products, tablets with the same manufacturing lot number were taken, and ground into a powder. The powders were divided into three batches and varying predetermined amounts of purified Shilajit powder (13 mg, 40 mg or 100 mg of Shilajit (Dabur India Limited, New Delhi, India) per tablet) were added to each batch. The powders were then repressed into tablets, in such a way that each retained all of its original ingredients in the same quantities plus 13 mg of Shilajit, 40 mg of Shilajit, or 100 mg of Shilajit per tablet. As controls, samples of each formula, from the same manufacturing lot number as those ground and mixed with Shilajit, were retained and re-tabletted. Thus, four samples of each formulation were obtained for testing purposes, each sample containing identical amounts of the same active ingredients (vitamins and minerals), with the exception that one sample contained no Shilajit; the second sample contained 13 mg per tablet of Shilajit; the third sample contained 40 mg per tablet of Shilajit; and the fourth sample contained 100 mg per tablet of Shilajit.

The results of testing of each of the four samples of the five formulations with the Cameron Aurometer are shown in Table 8.

As shown in Table 8, the addition of small amounts of purified Shilajit powder to vitamin-mineral tablets enhances the energetic properties of the tablets. It was also found that 10 grams of purified Shilajit powder caused the Aurometer to oscillate with an amplitude of 5 centimeters. Thus, the evidence suggests that the energy field of any combined vitamin-mineral-Shilajit tablet is stronger than either (a) the energy field of the equivalent vitamin-mineral tablet without Shilajit, or (b) the energy field of Shilajit itself.

EXAMPLE 2

The energetic response of subjects to Shilajit-containing compounds was measured using a Colight Body Ratio Analyzing Instrument, supplied by the Electro-Medica Office, Rexdale, Ontario. The instrument is an electronic resonance device which measures subtle energetic frequency characteristics of the human body. It consists of a series of potentiometers connected to the subject by means of a galvanic plate held against the skin.

In particular, the energetic response of five healthy subjects to each of the five different formulations shown in Tables 2-6 was measured. The subjects chosen were as follows: #1 - Male, aged 47; #2 -Female, aged 47; #3- Male, aged 37; #4 -Male, aged 54; and #5 - Male, aged 25. The subjects were administered the four samples (containing no Shilajit, 13 mg, 40 mg, or 100 mg of Shilajit per tablet) of each of the five formulations as described in Example 1. Each set of tablets was enclosed in a thin, opaque paper envelope, blinded from both the subject and the Colight operator.

Although the Colight machine is capable of measuring the electronic resonance of many bodily cells, organs and systems, only the vitality of each subject being tested was measured. Vitality is an indication of the strength of biomagnetic energy expressed throughout the entire body. The vitality ratio for each subject was recorded at baseline, i.e. prior to administration of the samples. Each of the four samples of the five formulations were then placed against the skin of the subject and the vitality ratio of the subject was recorded for each of the twenty different samples. This allowed a measurement of how the energy field of the subject would respond to the energy field of the various tablets.

The results are shown in Table 9. The vitality ratio, as measured by the Colight instrument, has a normal range of from 60 to 85, according to literature published by the Electro Medica Office. The results in Table 9 show that the various samples of the vitamin-mineral formulations without Shilajit increased the vitality readings of the subjects, on average, by 2.0%. In every case, the samples of the vitamin-mineral formulations with Shilajit increased the vitality reading of each subject beyond that of the vitality readings of the same sample formulations without Shilajit. Finally, the various samples of vitamin-mineral formulations with Shilajit increased the vitality readings of the subjects, on average, by 10.6%.

The vitality or strength of biomagnetic energy of the tablets themselves without reference to the energy field of any person was also measured using the Colight Body Ratio Analyzing Instrument and the results are shown in Table 10. As shown in Table 10 no detectable vitality was measured by this method in any of the vitamin-mineral formulations that do not contain Shilajit. Adding Shilajit to these formulations gives them a vitality reading at or near that of pure Shilajit itself. The vitality readings of the enhanced formulations are approximately the same, regardless of how much Shilajit is added to each formulation.

EXAMPLE 3

The refractive index of Shilajit-containing preparations was measured using an Abbé Refractometer, Type I, manufactured by Atago. The refractive index of a substance is the ratio of the velocity of light in air to the velocity of light in the substance. All measurements were taken at 24 degrees Celsius. At this temperature, the refractive index for water is 1.3326 and 1.3624 for alcohol.

The purpose of this test was to determine whether Shilajit improved the ability of an alcohol solution of a vitamin-mineral composition to transmit light. The refractive index of an alcohol solution of each of the five formulations set out in Tables 2 to 6 without Shilajit was measured, and compared with the refractive index of alcohol solutions of FORMULA C.N.R. (Table 5) with 13 mg of Shilajit; FORMULA V.S.C. (Table 2) with 40 mg of Shilajit; SUPER C-M-K (Table 6) with 40 mg of Shilajit; FORMULA S.T.R. (Table 3) with 40 mg of Shilajit; and, ORIGINAL FORMULA (Table 4) with 40 mg of Shilajit.

To prepare the alcohol solutions ten tablets of each of the formulations to be tested were crushed and two grams of each of the resultant powders were taken and extracted with isopropyl alcohol to make a 10% solution.

The results are shown in Table 11. In every case, Shilajit lowered the refractive index of the vitamin-mineral formulation. In other words, the addition of Shilajit improved the ability of the alcohol solution of each of the vitamin-mineral formulations to transmit light.

EXAMPLE 4

The effect of Shilajit on the transmission of infrared light by a vitamin-mineral formulation was measured using an Infrared Spectrophotometer. This instrument produces a visual graph of varying percentages of transmission at different wave lengths of infrared light.

Ten percent alcohol solutions of each of the formulations to be tested were prepared as described in Example 3 and their ability to transmit infrared light was measured using a Perkin-Elmer 1310 Infrared spectrophotometer. The results are shown in FIGS. 1 to 10. Because the machine may start at a different setting for each printout, the graphs are a relative or comparative form of measurement, rather than an absolute one. Therefore, when comparing the graphs for two different samples of the same formula, the shape of the curves is significant but the absolute measurement on the left-hand scale is not. For the same reason, the absolute numbers on the left-hand scale are not significant when comparing two readings on different curves, whereas the difference between two readings on the same curve are significant.

In comparing the graphs for the ORIGINAL FORMULA, more peaks reached far higher for the formulation containing 13 mg of Shilajit per tablet (FIG. 2) than for the one with no Shilajit (FIG. 1). The latter curve (FIG. 1) is very flat, with low plateaus rather than peaks. Similar relationships were found when comparing S.T.R. with 13 (FIG. 4) and 40 mg (FIG. 5) of Shilajit, whose curves show very high peaks, to S.T.R. without Shilajit (FIG. 3), which is very flat with low plateaus.

The curves for SUPER C.M.K. with 40 (FIG. 7) and 13 mg (FIG. 8) of Shilajit are almost identical, with high peaks, in the range of 4,000 to 1,600 $cm^{-1}$, compared to the curve for SUPER C.M.K. without Shilajit (FIG. 6) over the same range, which is almost completely flat.

Figure 9:
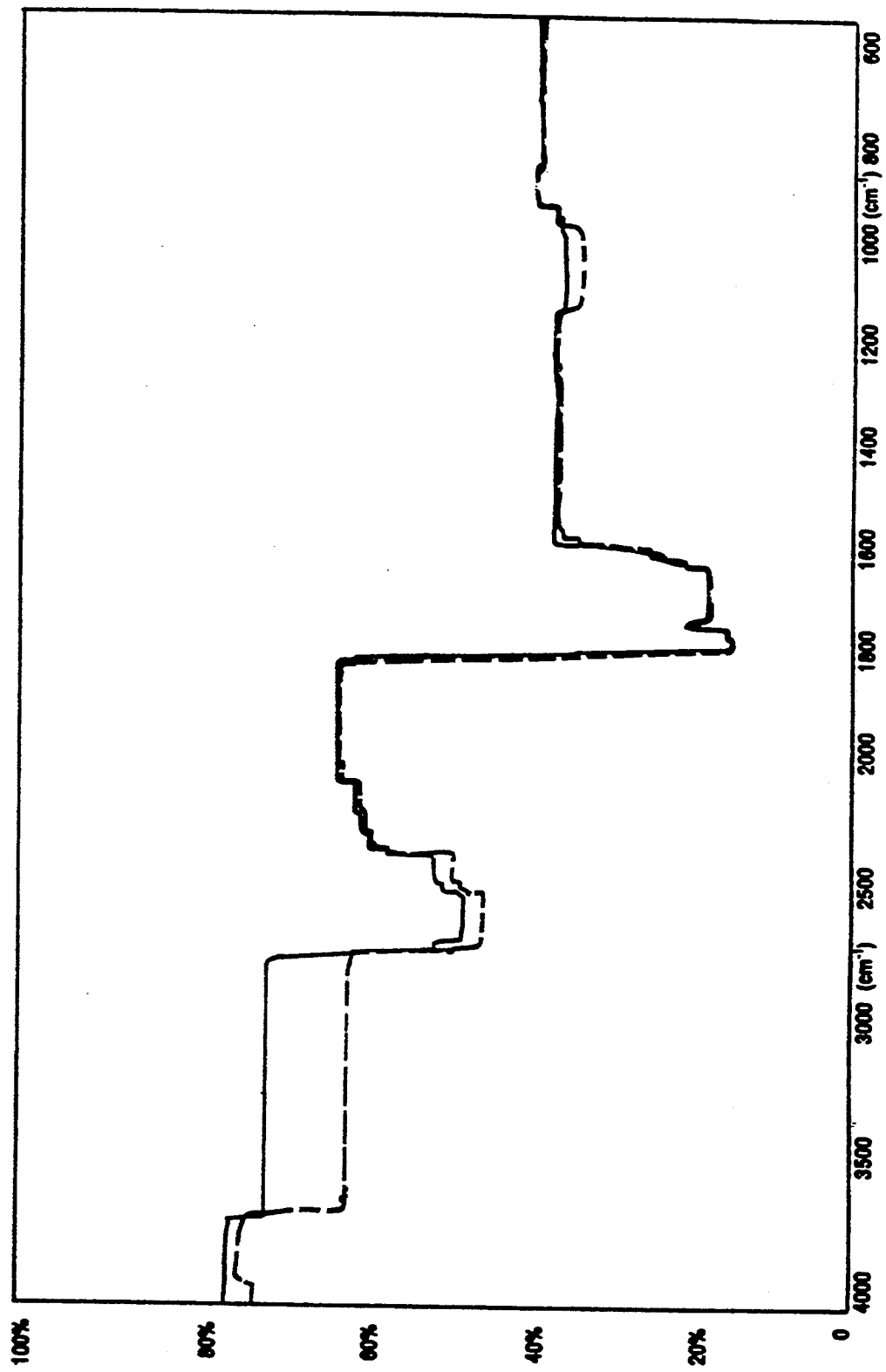
FIG. 9 is a gragh showing the transmission of infrared light by a sample containing the components of the Formula C.N.R. vitamin-mineral formulation and by a sample containing the components of the Formula C.N.R. vitamin-mineral formulation and 13 mg of Shilajit.
Figure 10:
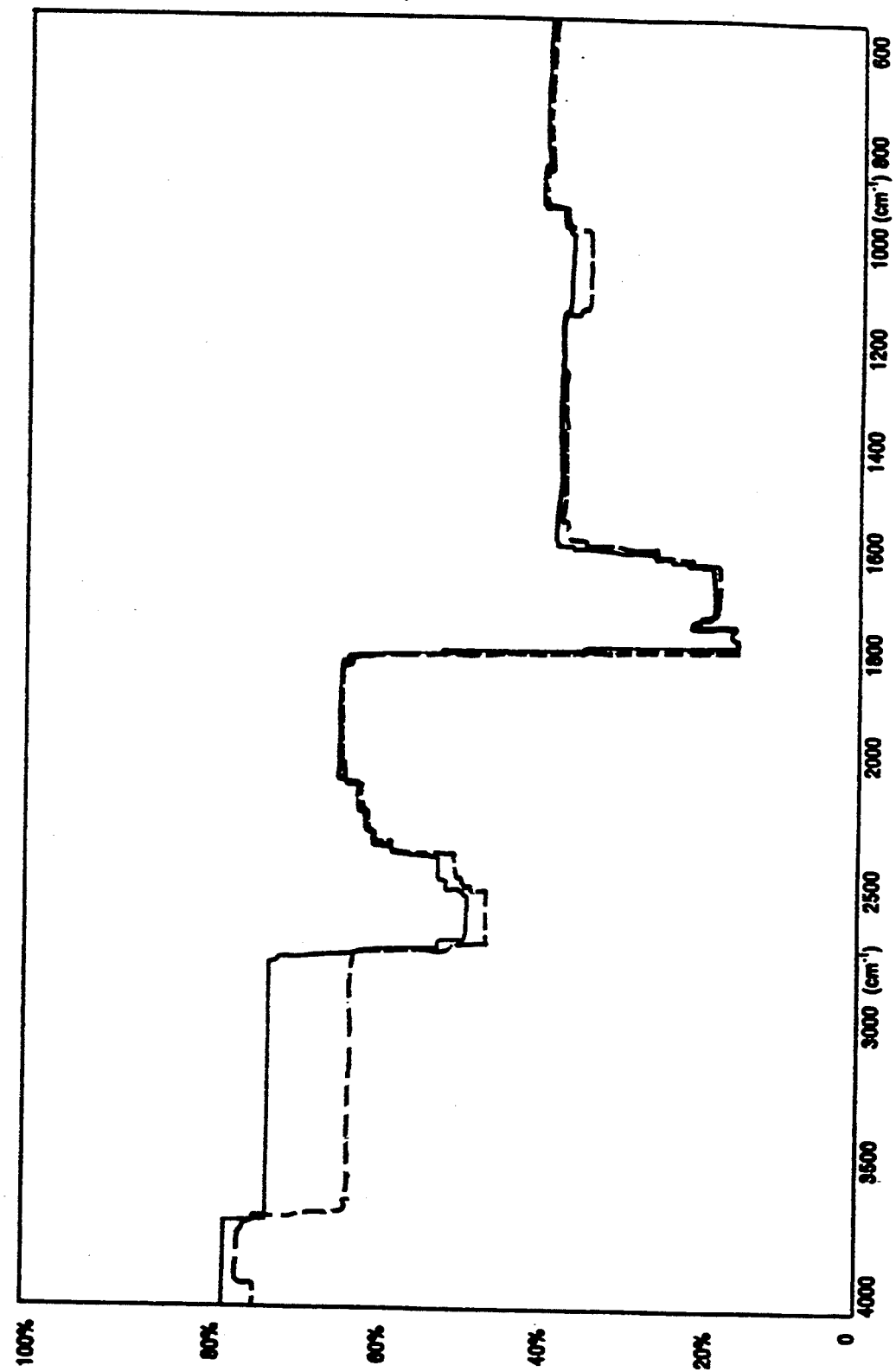
FIG. 10 is a gragh showing the transmission of infrared light by a sample containing the components of the Formula V.S.C. vitamin-mineral formulation and by a sample containing the components of the Formula V.S.C. vitamin-mineral formulation and 13 mg of Shilajit.

Samples of Formula C.N.R. with and without Shilajit and samples of Formula V.S.C. with and without Shilajit were run simultaneously. The results of the C.N.R. without Shilajit and with 13 mg of Shilajit are shown in FIG. 9 and the results of the V.S.C. without Shilajit and with 13 mg of Shilajit are shown in FIG. 10. In both cases, the samples of the formulations with 13 mg of Shilajit were found to transmit about 10% more infrared light over the range of 3500 to 2700 $cm^{-1}$ when compared to the samples without Shilajit, and approximately 2% more in the ranges from 2760 to 2300 $cm^{-1}$ and from 1150 to 1000 $cm^{-1}$.

The results indicate that the addition of Shilajit to otherwise identical vitamin-mineral formulations was found to improve the ability of these formulations to transmit infrared light.

EXAMPLE 5

Paper chromatography was used to analyze samples of the vitamin/mineral formulations set out in Tables 1 to 5 with or without Shilajit. Paper chromatography is a qualitative method used for separating and identifying mixtures of substances, including vitamins and food products. The method is useful for discerning subtle differences in vitamins and food samples produced by different processing methods or from different soil conditions - differences which are not detectable by quantitative assay.

The method described in Pfeiffer, E. E. Chromatography Applied to Quality Testing, Wyoming: Biodynamic Literature, 1984 was used to analyze samples of the vitamin/mineral formulations set out in Tables 2 to 6 with or without Shilajit. The method generally involves preparing a filter disk with a 0.1% silver nitrate solution, and impregnating the prepared disk with a liquid extract of the test sample in a 0.1% sodium hydroxide solution. This method results in the formation of various colour zones and patterns which reflect certain aspects of sample quality.

Much work has been done with paper chromatography in comparing synthetic vitamins to natural source vitamins, and in comparing organic produce to that produced by conventional agricultural methods. (Pfeiffer, Ibid.) In both of these kinds of comparisons, the natural/organic versions display colours and patterns which are more distinct, deeper and more vibrant than their synthetic or conventional counterparts. Also, there are more pronounced boundaries and more clearly defined radial spokes in the natural/organic substances.

Chromatograms of samples containing each of Formula STR, ORGINAL, CNR, CMK and VSC without Shilajit and with Shilajit are shown in FIGS. 11 to 15. As shown in FIGS. 11 to 15 the samples with Shilajit (FIGS. 11A, 12A, 13A, 14A and 15A) produce colour images which are more vibrant, more distinct, and with more clearly defined borders and more obvious radial spokes than the samples without Shilajit (FIGS. 11B, 12B, 13B, 14B and 15B). These qualitative differences suggest an enhanced energy quality for the samples with Shilajit compared to those without.

Figures 11A, 11B:
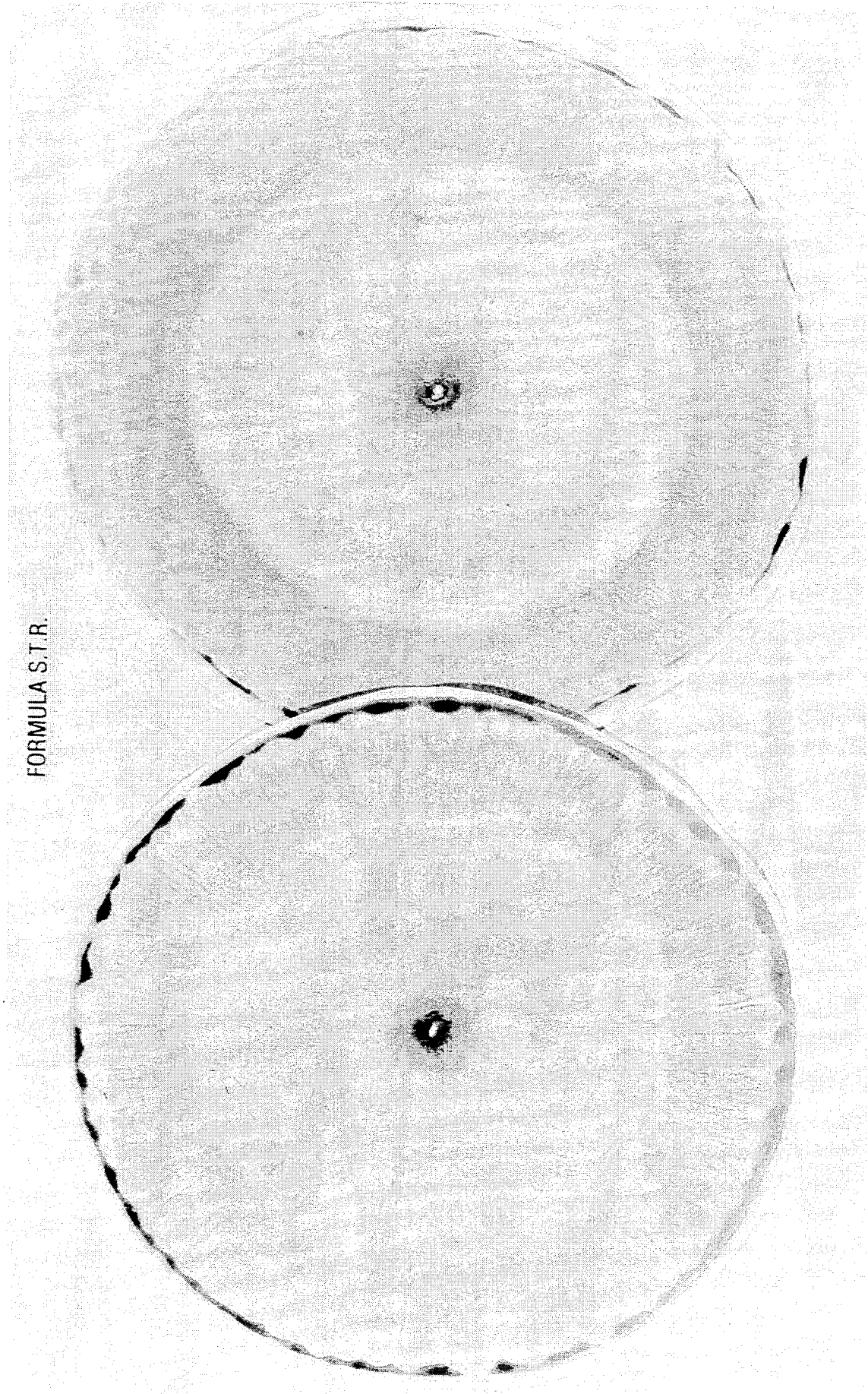
FIG. 11 are chromatograms of alcohol solutions of the components of the Formula S.T.R. vitamin-mineral formulation with (FIG. 11A) and without (FIG. 11B) Shilajit.

In particular, the presence of the vitamins and minerals in Formula S.T.R. give the paper disk its characteristic colours of reddish-brown, green, yellow and brown (going from the centre to the perimeter) (FIG. 11B). In the enhanced Shilajit version, however, the rings of colour are deeper, more clearly defined and more vibrant (FIG. 11A). There is an extra ring of a deep blue (almost cobalt blue) in the Shilajit enhanced formula that is not in the STR without Shilajit. The outside brown border is wider in the Shilajit version. There is also an obvious spoke pattern interspersed with glimpses of the very light yellow (almost white) colour that does not appear in the STR without Shilajit.

Figures 12A, 12B:
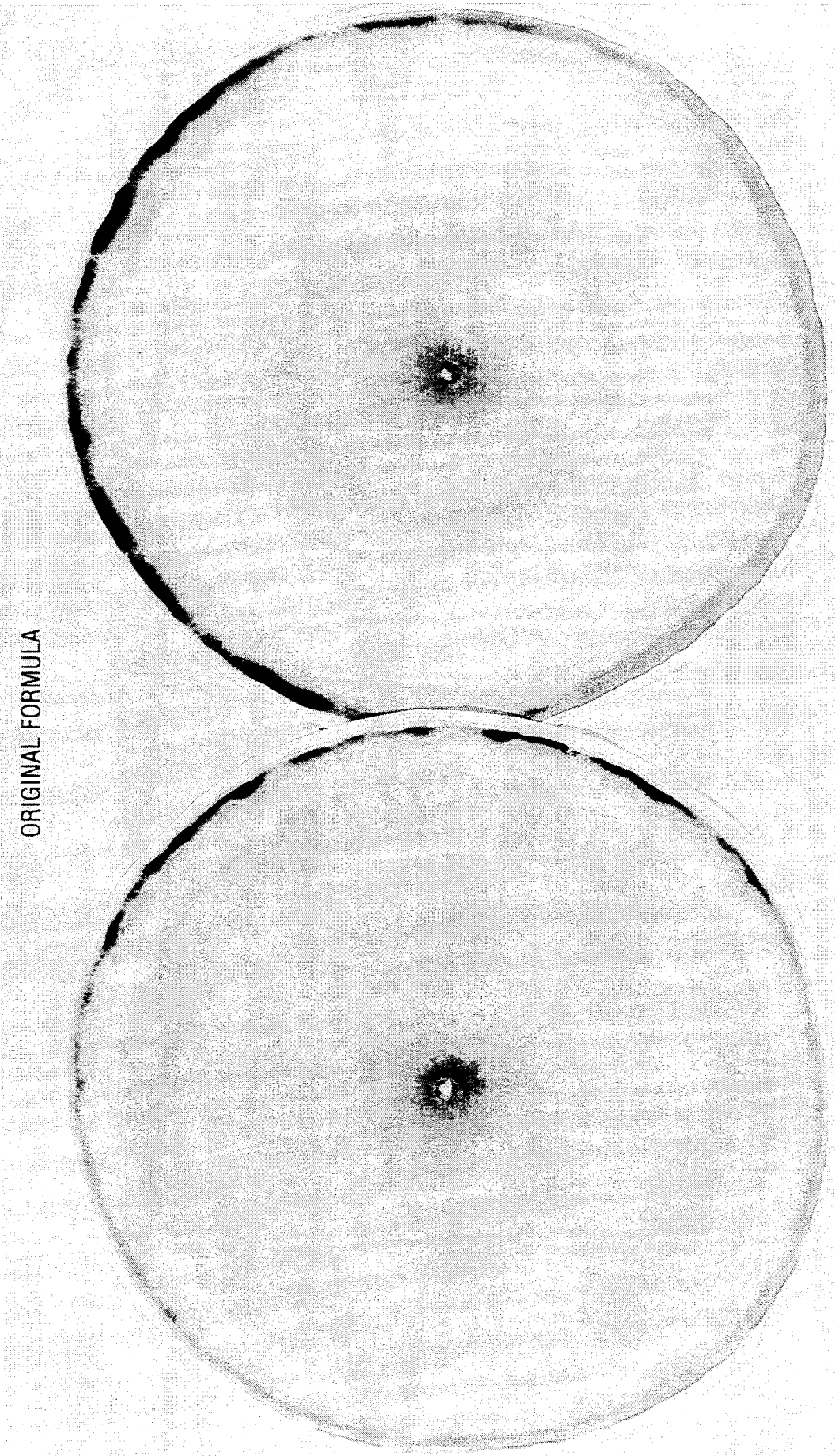
FIG. 12 are chromatograms of alcohol solutions of the components of the Original Formula vitamin-mineral formulation with (FIG. 12A) and without (FIG. 12B) Shilajit.

The Shilajit enhanced version of the Original formula (FIG. 12A) displays a distinct pattern of colours, spokes and rings that are quite different from the version without Shilajit (FIG. 12B).

Figures 13A, 13B:
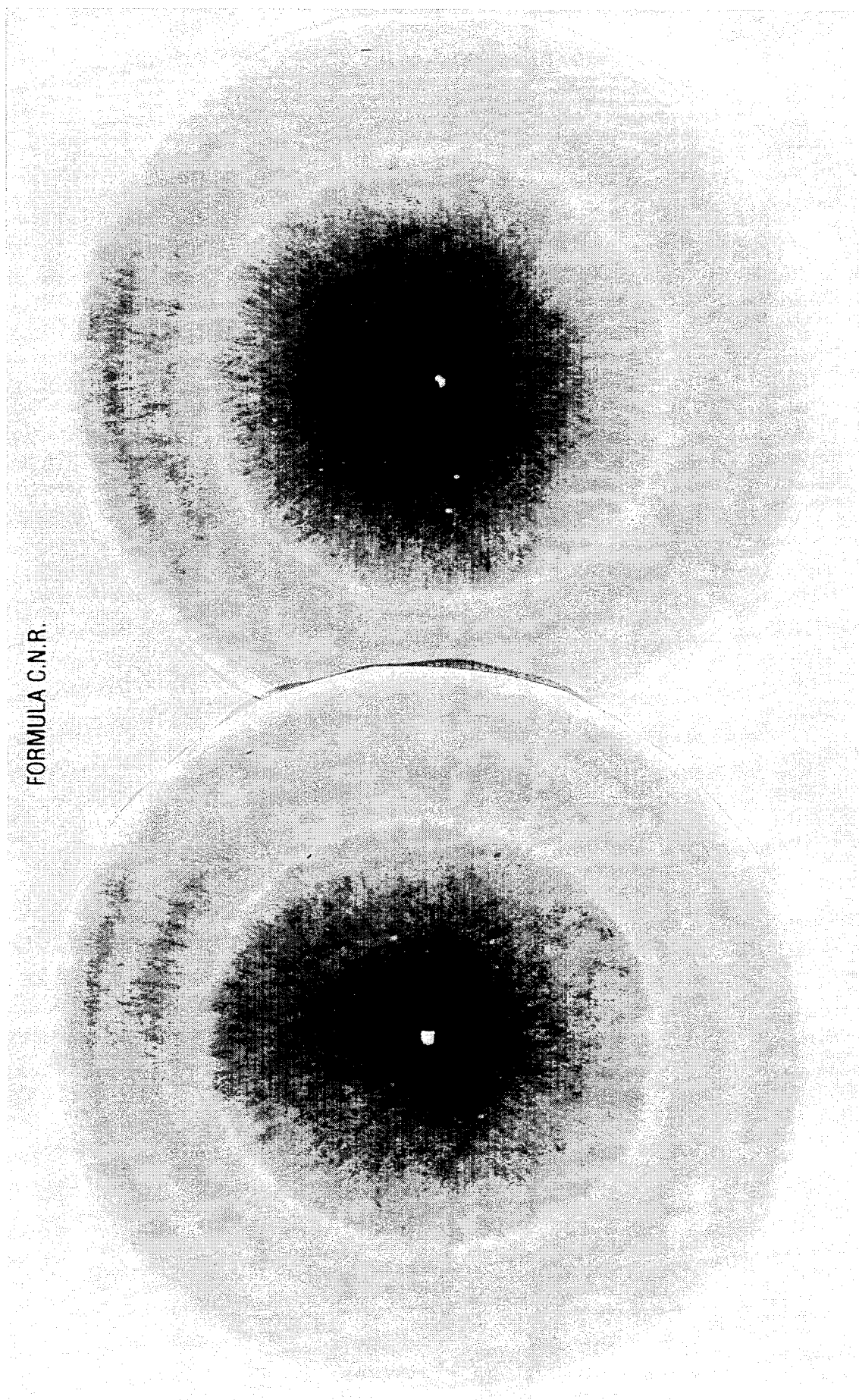
FIG. 13 are chromatograms of alcohol solutions of the components of the Formula C.N.R. vitamin-mineral formulation with (FIG. 13A) and without (FIG. 13B) Shilajit.

The differences between the two samples of the C.N.R. formula are more subtle, but they exist nevertheless. The outermost brown border is darker and more distinct for the version with Shilajit (FIG. 13A). There is a thin, brown ring about one quarter inch inside the perimeter in the version with Shilajit which is not apparent in the version without Shilajit (FIG. 13B). Also, the green colour and its fine spoke pattern is more distinct in the version with Shilajit.

Figures 14A, 14B:
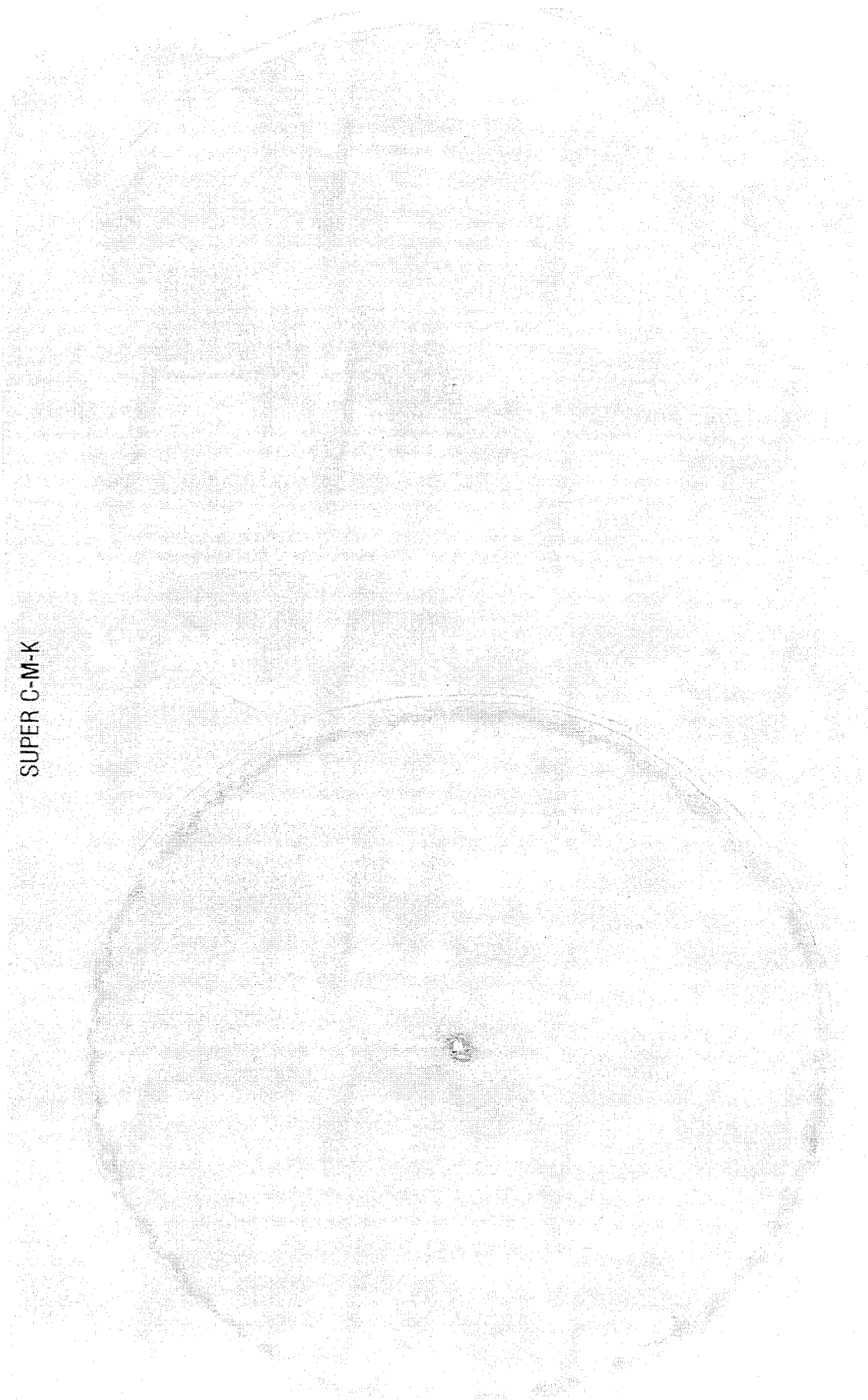
FIG. 14 are chromatograms of alcohol solutions of the components of the Formula SUPER C-M-K vitamin-mineral formulation with (FIG. 14A) and without (FIG. 14B) Shilajit.

The colour of the original paper disk for the Super C-M-K without Shilajit is a whitish gray (FIG. 14B). This is so because the only active ingredients in this formula are calcium, magnesium and potassium. There are no vitamins present that would contribute the spectrum of colours visible in the other formulations. The enhanced C-M-K with Shilajit, however, has a more distinct yellow perimeter than the C-M-K without Shilajit (FIG. 14A). The enhanced Shilajit sample also has an obvious and distinct brown border (inside the outer yellowish one) which is almost totally lacking in the sample without Shilajit. The centre of the Shilajit enhanced sample contains a bluish-brown stain that is several times larger and many times more distinct than a very faint hint of such a stain in the sample without Shilajit.

Figure 15A:
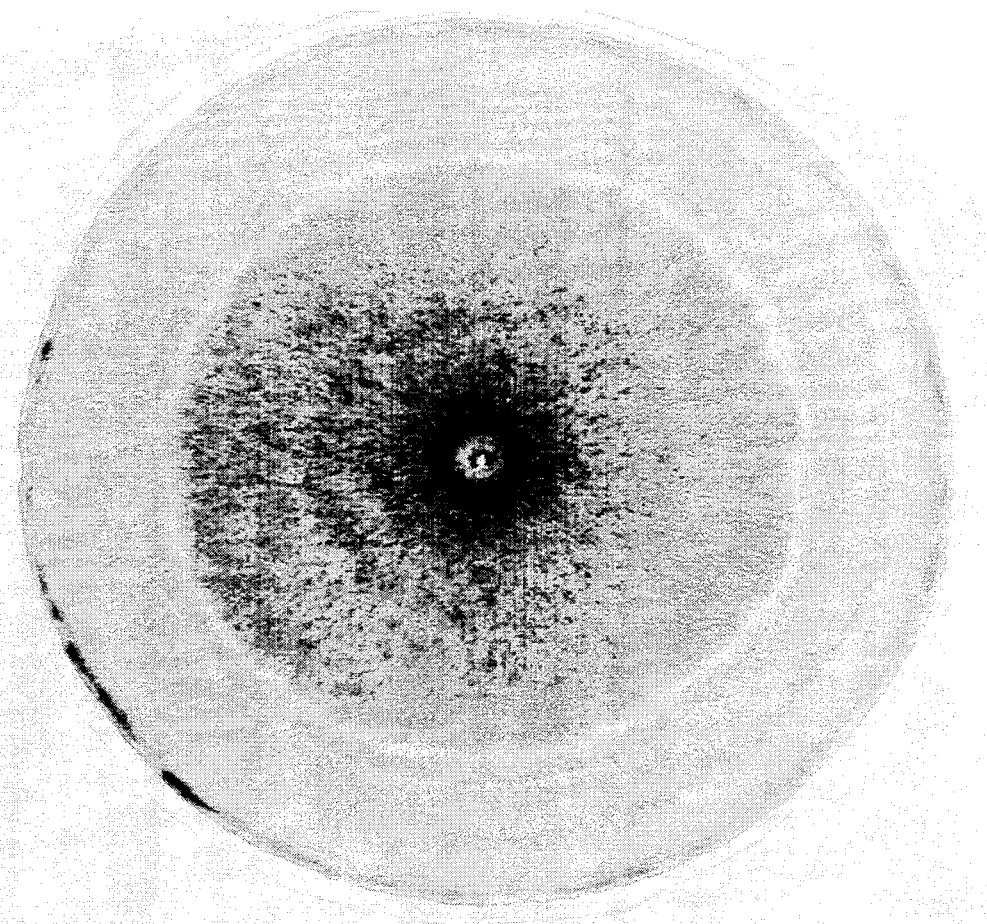
FIG. 15 are chromatographs of alcohol solutions of the components of the Formula V.S.C. vitamin-mineral formulation with (FIG. 15A) and without (FIG. 15B) Shilajit.
Figure 15B:
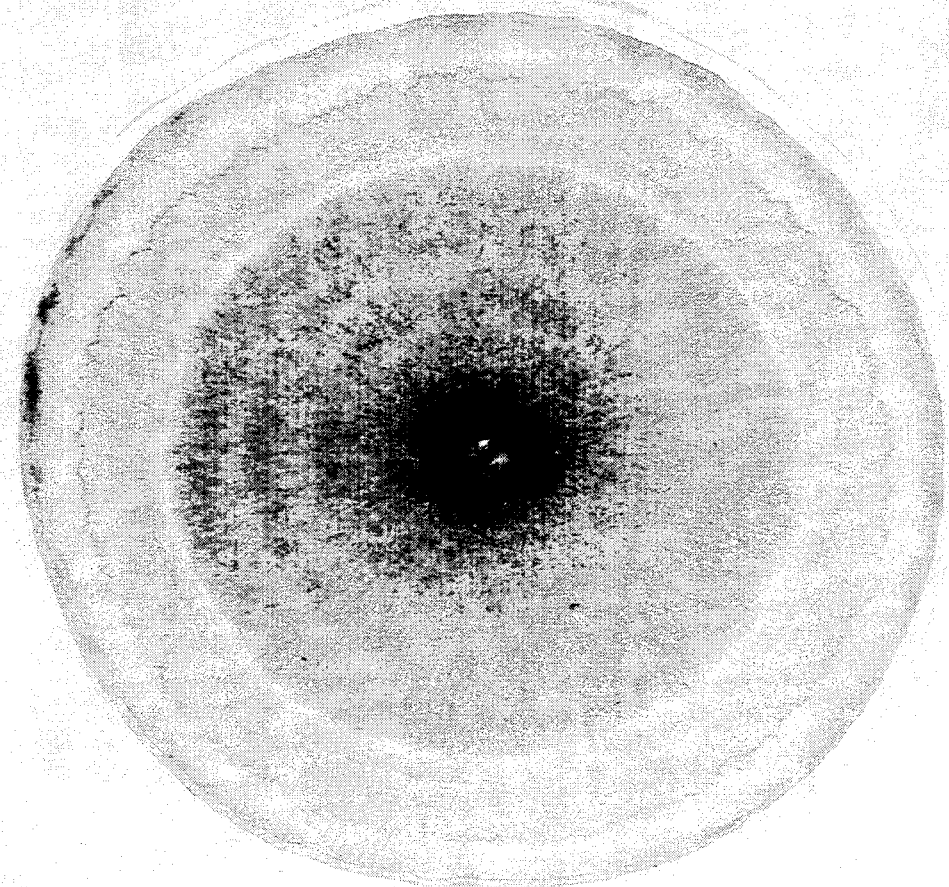

The boarders of the colours in the Shilajit enhanced sample of the V.S.C. formula are more clear and distinct (FIG. 15A) than in the version without Shilajit (FIG. 15B). In this latter version, the colours seem to wander or spill over from one ring to the next.

TABLE 1

|  | Each Tablet contains |
|---|---|
| Vitamin A | 500 to 10,000 I.U. |
| Beta Carotene | 2,000 to 15,000 I.U. |
| Vitamin D | 50 to 400 I.U. |
| Vitamin E | 30 to 400 I.U. |
| Vitamin C | 75 to 1,000 mg |
| Vitamin B-1 | 2 to 80 mg |
| Vitamin B-2 | 1 to 80 mg |
| Niacin | 4 to 100 mg |
| Niacinamide | 2 to 100 mg |
| Pantothenic Acid | 10 to 500 mg |
| Vitamin B-6 | 3 to 100 mg |
| Folic Acid | 0.002 to 1 mg |
| Vitamin B-12 | 3 to 1,000 mcg |
| Biotin | 3 to 80 mcg |
| Calcium | 40 to 200 mg |
| Magnesium | 30 to 200 mg |
| Potassium | 10 to 200 mg |
| Iron | 1 to 25 mg |
| Iodine | 0.02 to 0.5 mg |
| Manganese | 0.8 to 6 mg |
| Zinc | 1.5 to 30 mg |
| Chromium | 10 to 80 mcg |
| Selenium | 20 to 50 mcg |

TABLE 2

VITAMOST ® Formula V.S.C.

|  | Each Tablet contains |
|---|---|
| Vitamins |  |
| Vitamin A (fish liver oil) | 2,000 I.U. |
| Beta Carotene (pro-vitamin A) | 6,000 I.U. |
| Vitamin E (d-alpha tocopheryl succ.) | 60 I.U. |
| Vitamin C (calcium ascorbate) | 150 mg |
| Vitamin C (ascorbic acid) | 350 mg |
| Vitamin B-1 (thiamine hydrochloride) | 2 mg |
| Vitamin B-2 (riboflavin) | 1 mg |
| Vitamin B-6 (pyridoxine hydrochloride) | 3 mg |
| Vitamin B-12 (cobalamin) | 3 mcg |
| Niacin | 4 mg |
| Niacinamide | 2 mg |
| Panthothenic Acid (d-calc. pantothen.) | 2 mg |
| Folic Acid | 0.03 mg |
| Biotin | 3 mcg |
| Lipotropic Factors |  |
| Choline (bitartrate) | 40 mg |
| Inositol | 10 mg |
| dl-Methionine | 100 mg |
| Minerals |  |
| Magnesium (oxide) | 30 mg |
| Potassium (citrate) | 10 mg |
| Manganese (gluconate) | 1 mg |
| Zinc (gluconate) | 1.5 mg |
| Chromium (proteinate) | 20 mcg |
| Selenium (proteinate) | 20 mcg |
| Non-Medicinal Ingredients |  |
| Betaine Hydrochloride | 12 mg |
| Lemon Bioflavanoids | 15 mg |
| l-Cysteine Hydrochloride | 75 mg |
| Lecithin | 10 mg |
| Thymus concentrate | 3 mg |
| Spleen concentrate | 3 mg |
| Adrenal concentrate | 3 mg |

TABLE 3

VITAMOST ® Formula S.T.R.

| | Each Tablet contains |
|---|---|
| Vitamins | |
| Vitamin A (fish liver oil) | 2,500 I.U. |
| Vitamin D (fish liver oil) | 100 I.U. |
| Vitamin E (d-alpha tocopheryl succinate) | 40 I.U. |
| Vitamin C (ascorbic acid) | 200 mg |
| Vitamin B-1 (thiamine hydrochloride) | 5 mg |
| Vitamin B-2 (riboflavin) | 5 mg |
| Vitamin B-6 (pyridoxine hydrochloride) | 10 mg |
| Vitamin B-12 (cobalamin) | 50 mcg |
| Niacinamide | 5 mg |
| Pantothenic Acid (d-calcium pantothenate) | 150 mg |
| Folic Acid | 0.04 mg |
| Biotin | 10 mcg |
| Lipotropic Factors | |
| Choline (bitartrate) | 10 mg |
| Inositol | 10 mg |
| Minerals | |
| Calcium (carbonate) | 50 mg |
| Magnesium (oxide) | 35 mg |
| Potassium (chloride) | 40 mg |
| Iron (ferrous fumarate) | 1.5 mg |
| Iodine (potassium iodide) | 0.0225 mg |
| Manganese (gluconate) | 2 mg |
| Zinc (gluconate) | 1.5 mg |
| Chromium (proteinate) | 20 mcg |
| Selenium (proteinate) | 20 mcg |
| Non-Medicinal Ingredients | |
| Para Amino Benzoic Acid (P.A.B.A) | 5 mg |
| Betaine Hydrochloride | 15 mg |
| Lemon Bioflavanoids | 20 mg |
| Adrenal concentrate | 10 mg |

TABLE 4

VITAMOST ® Original Formula

| | Each Tablet contains |
|---|---|
| Vitamins | |
| Vitamin A (fish liver oil) | 4,167 I.U. |
| Vitamin D (fish liver oil) | 167 I.U. |
| Vitamin E (d-alpha tocopheryl succinate) | 66.7 I.U. |
| Vitamin C (ascorbic acid) | 200 mg |
| Vitamin B-1 (thiamine hydrochloride) | 10 mg |
| Vitamin B-2 (riboflavin) | 10 mg |
| Vitamin B-6 (pyridoxine hydrochloride) | 10 mg |
| Vitamin B-12 (cobalamin) | 16.7 mcg |
| Niacinamide | 10 mg |
| Pantothenic Acid (d-calcium pantothenate) | 20 mg |
| Folic Acid | 0.067 mg |
| Biotin | 16.7 mg |
| Lipotropic Factors | |
| Choline (bitartrate) | 10 mg |
| Inositol | 10 mg |
| Minerals | |
| Calcium (carbonate) | 167 mg |
| Magnesium (oxide) | 66.7 mg |
| Potassium (chloride) | 16.5 mg |
| Iron (ferrous fumarate) | 3 mg |
| Iodine (potassium iodide) | 0.038 mg |
| Manganese (gluconate) | 3 mg |
| Zinc (gluconate) | 3 mg |
| Chromium (proteinate) | 33.3 mcg |
| Selenium (proteinate) | 25 mcg |
| Non-Medicinal Ingredients | |
| Para Amino Benzoic Acid (P.A.B.A) | 10 mg |
| Betaine Hydrochloride | 20 mg |
| Lemon Bioflavanoids | 20 mg |

TABLE 5

VITAMOST ® Formula C.N.R.

| | Each Tablet contains |
|---|---|
| Vitamins | |
| Beta Carotene (pro-vitamin A) | 15,000 I.U. |
| Vitamin C (calcium ascorbate) | 835 mg |
| Lipotropic Factors | |
| dl-Methionine | 5 mg |
| Mineral | |
| Selenium (proteinate) | 25 mcg |
| Non-Medicinal Ingredients | |
| Glutathione | 1.3 mg |
| N,N-Dimethylglycine | 8 mg |

In a non-medicinal base containing Echinacea, Red Clover, Liver concentrate, Thymus concentrate, Damiana, Burdock, Marshmallow, Spleen concentrate, Elecampagne and Buckthorn.
The product contains no sugar, no starch, no colourings, no flavourings, no preservatives, no milk, no wheat, no corn, no gluten, no soy, no yeast.

TABLE 6

VITAMOST ® Super C-M-K

| | Each Tablet contains |
|---|---|
| Vitamins | |
| Calcium (carbonate) | 200 mg |
| Magnesium (oxide) | 200 mg |
| Potassium (chloride) | 200 mg |

The product contains no sugar, no starch, no colourings, no flavourings, no preservatives, no milk, no gluten, no corn, no soy, and no yeast.

TABLE 7

Composition of Shilajit*

| | Amount (per cent) |
|---|---|
| Organic | |
| Moisture | 29.03 |
| Benzoic acid | 8.58 |
| Hippuric acid | 6.13 |
| Fatty acids | 1.36 |
| Resin and waxy matter | 2.44 |
| Gums | 17.32 |
| Albuminoids | 16.12 |
| Vegetable matter, sand, etc. | 2.15 |
| Minerals** | |
| Loss on ignition | 52.63 |
| Ash | 18.34 |
| Silica (residue insoluble in HCl) | 2.69 |
| Iron ($Fe_2O_3$) | 0.64 |
| Alumina ($Al_2O_3$) | 2.61 |
| Lime (CaO) | 4.82 |
| Magnesia (MgO) | 1.20 |
| Potash ($K_2O$) | 3.81 |
| Sulphuric acid ($SO_3$) | 0.97 |
| Chloride (NaCl) | 0.57 |
| Phosphoric acid ($P_2O_5$) | 0.24 |
| Nitrogen | 3.36 |

*From the Indian Materia Medica, pages 25 and 26.
**Mineral constituents obtained from the ash by incineration of the substance at a dull red heat.

TABLE 8

| Product | Shilajit/ Tablet | No. of Tablets | Aurameter Stroke |
|---|---|---|---|
| SUPER C-M-K | 0 | 4 | 3 cm |
| SUPER C-M-K | 13 mg | 4 | 7 cm |
| SUPER C-M-K | 40 mg | 4 | 7 cm |
| SUPER C-M-K | 100 mg | 4 | 7 cm |
| FORMULA C.N.R. | 0 | 12 | 3 cm |
| FORMULA C.N.R. | 13 mg | 12 | 6 cm |
| FORMULA C.N.R. | 40 mg | 12 | 6 cm |
| FORMULA C.N.R. | 100 | 12 | 6 cm |
| ORIGINAL FORMULA | 0 | 6 | 3 cm |
| ORIGINAL FORMULA | 13 mg | 6 | 7 cm |
| ORIGINAL FORMULA | 40 mg | 6 | 7 cm |
| ORIGINAL FORMULA | 100 mg | 6 | 6 cm |
| FORMULA S.T.R. | 0 | 10 | 4 cm |

TABLE 8-continued

| Product | Shilajit/Tablet | No. of Tablets | Aurameter Stroke |
|---|---|---|---|
| FORMULA S.T.R. | 13 mg | 10 | 6 cm |
| FORMULA S.T.R. | 40 mg | 10 | 6 cm |
| FORMULA S.T.R. | 100 mg | 10 | 6 cm |
| FORMULA V.S.C. | 0 | 10 | 4 cm |
| FORMULA V.S.C. | 13 mg | 10 | 7 cm |
| FORMULA V.S.C. | 40 mg | 10 | 8 cm |
| FORMULA V.S.C. | 100 mg | 10 | 7 cm |

TABLE 9

| | Subject | | | | |
|---|---|---|---|---|---|
| | #1 | #2 | #3 | #4 | #5 |
| Baseline | 63 | 66 | 72 | 80 | 74 |
| Formula V.S.C. without Shilajit | 67 | 68 | 73 | 82 | 75 |
| Formula V.S.C. with 13 mg Shilajit | 77 | 81 | 78 | 86 | 77 |
| Formula V.S.C. with 40 mg Shilajit | 81 | 81 | 82 | 86 | 77 |
| Formula V.S.C. with 100 mg Shilajit | 73 | 74 | 79 | 83 | 80 |
| Baseline | 63 | 66 | 72 | 80 | 74 |
| Formula S.T.R. without Shilajit | 65 | 69 | 73 | 80 | 75 |
| Formula S.T.R. with 13 mg Shilajit | 80 | 75 | 76 | 81 | 76 |
| Formula S.T.R. with 40 mg Shilajit | 73 | 83 | 85 | 81 | 77 |
| Formula S.T.R. with 100 mg Shilajit | 78 | 74 | 75 | 84 | 81 |
| Baseline | 63 | 66 | 72 | 80 | 74 |
| Original Formula without Shilajit | 64 | 67 | 73 | 81 | 74 |
| Originial Formula with 13 mg Shilajit | 71 | 72 | 74 | 87 | 79 |
| Originial Formula with 40 mg Shilajit | 71 | 70 | 78 | 84 | 79 |
| Originial Formula with 100 mg Shilajit | 72 | 77 | 75 | 90 | 78 |
| Baseline | 63 | 66 | 72 | 80 | 74 |
| Formula C.N.R. without Shilajit | 64 | 68 | 78 | 80 | 74 |
| Formula C.N.R. with 13 mg Shilajit | 75 | 75 | 85 | 82 | 77 |
| Formula C.N.R. with 40 mg Shilajit | 81 | 78 | 85 | 84 | 81 |
| Formula C.N.R. with 100 mg Shilajit | 71 | 77 | 83 | 81 | 78 |
| Baseline | 63 | 66 | 72 | 80 | 74 |
| Super C-M-K without Shilajit | 63 | 69 | 72 | 82 | 75 |
| Super C-M-K with 13 Shilajit | 72 | 75 | 79 | 84 | 77 |
| Super C-M-K with 40 mg Shilajit | 72 | 74 | 78 | 83 | 77 |
| Super C-M-K with 100 mg Shilajit | 66 | 72 | 84 | 84 | 78 |

TABLE 10

| | Vitality Reading |
|---|---|
| Pure Shilajit | 41 |
| Formula VSC without Shilajit | 0 |
| Formula VSC with 13 mg Shilajit | 41 |
| Formula VSC with 40 mg Shilajit | 43 |
| Formula VSC with 100 mg Shilajit | 41 |
| Formula STR without Shilajit | 0 |
| Formula STR with 13 mg Shilajit | 42 |
| Formula STR with 40 mg Shilajit | 42 |
| Formula STR with 100 mg Shilajit | 41 |
| Original Formula without Shilajit | 0 |
| Original Formula with 13 mg Shilajit | 41 |
| Original Formula with 40 mg Shilajit | 37 |
| Original Formula with 100 mg Shilajit | 41 |
| Formula CNR without Shilajit | 0 |
| Formula CNR with 13 mg Shilajit | 42 |
| Formula CNR with 40 mg Shilajit | 42 |
| Formula CNR with 100 mg Shilajit | 38 |
| Super C-M-K without Shilajit | 0 |
| Super C-M-K with 13 mg Shilajit | 41 |
| Super C-M-K with 40 Shilajit | 40 |
| Super C-M-K with 100 mg Shilajit | 40 |

TABLE 11

| | Refractive Index |
|---|---|
| FORMULA C.N.R. with no Shilajit | 1.3690 |
| FORMULA C.N.R. with 13 mg of Shilajit | 1.3682 |
| FORMULA V.S.C. with no Shilajit | 1.3841 |
| FORMULA V.S.C. with 40 mg of Shilajit | 1.3680 |
| SUPER C-M-K with no Shilajit | 1.3634 |
| SUPER C-M-K with 40 mg of Shilajit | 1.3624 |
| FORMULA S.T.R. with no Shilajit | 1.3654 |
| FORMULA S.T.R. with 40 mg of Shilajit | 1.3644 |
| ORIGINAL FORMULA with no Shilajit | 1.3664 |
| ORIGINAL FORMULA with 40 mg of Shilajit | 1.3650 |

I claim:

1. A composition comprising iron Shilajit in a multi vitamin and/or mineral preparation in which the Shilajit makes up between 0.4 and 10 per cent by weight of the total composition, wherein the composition is in the form of a solid formulation for oral administration.

2. A composition as claimed in claim 1 wherein the multi vitamin and/or mineral preparation has the following components:

| | |
|---|---|
| Vitamin A | 500 to 10,000 I.U. |
| Beta Carotene | 2,000 to 15,000 I.U. |
| Vitamin D | 50 to 400 I.U. |
| Vitamin E | 30 to 400 I.U. |
| Vitamin C | 75 to 1,000 mg |
| Vitamin B-1 | 2 to 80 mg |
| Vitamin B-2 | 1 to 80 mg |
| Niacin | 4 to 100 mg |
| Niacinamide | 2 to 10 mg |
| Pantothenic Acid | 10 to 500 mg |
| Vitamin B-6 | 3 to 100 mg |
| Folic Acid | 0.002 to 1 mg |
| Vitamin B-12 | 3 to 1,000 mcg |
| Biotin | 3 to 80 mcg |
| Calcium | 40 to 200 mg |
| Magnesium | 30 to 200 mg |
| Potassium | 10 to 200 mg |
| Iron | 1 to 25 mg |
| Iodine | 0.02 to 0.5 mg |
| Manganese | 0.8 to 6 mg |
| Zinc | 1.5 to 30 mg |
| Chromium | 10 to 80 mcg |
| Selenium | 20 to 50 mcg |

3. A composition as claimed in claim 1, wherein the Shilajit is present in a concentration of from about 1-3% by weight of the composition.

4. A composition as claimed in claim 1, wherein the multi vitamin and/or mineral preparation comprises Vitamin A and Vitamin C.

5. A composition as claimed in claim 1, wherein the multi vitamin and/or mineral preparation comprises Vitamin A and Vitamin C and selenium.

6. A composition as claimed in claim 1 wherein the multi vitamin and/or mineral preparation comprises Vitamin A, Vitamin D, Vitamin E, Vitamin C, Vitamin B, Niacinamide, Pantothenic Acid, Folic Acid, Calcium, Magnesium, Potassium, Manganese, Zinc, and/or Selenium.

7. A composition comprising iron Shilajit in a multi vitamin and/or mineral preparation wherein the Shilajit is present in a concentration of between 0.4 and 10.0 per cent of the total weight of the composition and the multi vitamin and/or mineral preparation comprises vitamin A, Vitamin D, Vitamin E, Vitamin C, Vitamin B, Niacinamide, Pantothenic Acid, Folic Acid, Calcium, Magnesium, Potassium, Manganese, Zinc, and/or Selenium, and wherein the composition is in the form of a solid formulation for oral administration.

* * * * *